United States Patent [19]

Baader et al.

[11] Patent Number: 5,519,038

[45] Date of Patent: May 21, 1996

[54] N,N'-BIS(ALKOXYALKYL)-PYRIDINE-2,4-DICARBOXYLIC ACID DIAMINES

[75] Inventors: Ekkehard Baader, Königstein/Taunus; Martin Bickel, Bad Homburg; Volkmar Günzler-Pukall, Marburg, all of Germany

[73] Assignee: Hoechst Aktiengesellschaft, Frankfurt am Main, Germany

[21] Appl. No.: 401,284

[22] Filed: Mar. 9, 1995

Related U.S. Application Data

[63] Continuation of Ser. No. 139,093, Oct. 21, 1993, abandoned, which is a continuation of Ser. No. 875,191, Apr. 27, 1992, abandoned, which is a continuation of Ser. No. 553,590, Jul. 18, 1990, abandoned.

[30] Foreign Application Priority Data

Jul. 20, 1989 [DE] Germany ............... 39 24 093.2

[51] Int. Cl.⁶ ................ C07D 213/30; A61K 31/44
[52] U.S. Cl. ........................................ 514/354; 546/323
[58] Field of Search ......................... 546/323; 514/354

[56] References Cited

U.S. PATENT DOCUMENTS 5,037,839  8/1991  Bickel et al. ............... 546/316

FOREIGN PATENT DOCUMENTS 88-0895  9/1988  South Africa .
88-0896  9/1988  South Africa .
88-1561  10/1988  South Africa .

OTHER PUBLICATIONS

Bickel CA 109:204933K same as South African pat. 88–0896, 1988.
Annoni, G. et al., Journal of Hepatology, vol. 2, pp. 379–388 (1986).
Babbs, C., et al., The Lancet, pp. 1021–1024 (May 7, 1988).
Gluud, C., et al., Hepatology, vol. 8, No. 2, pp. 222–227 (1988).
Annoni, G., et al., Hepatology, vol. 9, No. 5, pp. 693–697 (1989).
Gressner, A. M., et al., Clinica Chimica Acta, vol. 161, pp. 249–258 (1986).
Bolarin, D. M., et al., Eur. J. Clin. Invest, vol. 14, pp. 90–95 (1984).
Niemela, O., Gastroenterology, vol. 98, pp. 1612–1619 (1990).
Rhode, H., et al., Eur. J. Clinical Invest., vol. 9, pp. 451–459 (1979).
Hirayanma, C., et al., Biochem. J., vol. 118, pp. 229–232 (1970).
Kountrouras, J., et al., Br. J. Exp. Pathol., vol. 65, No. 3, pp. 305–311 (1984) (abstract).
Savolainen, E. R., et al., Alcohol. Clin. Exp. Res., pp. 384–389 (1984) (abstract).
Brocks, D. G., et al., Alcohol & Alcoholism, Suppl. 1, pp. 497–500 (1987).

Baader, E., et al, Hepatology, 4 Pt2, p. 247 (1990) (abstract).
Bickel, M., et al., Z. Gastroenterol, vol. 9, p. 536 (1989).
Galambos, M. R., et al., Hepatology, pp. 38–42 (1985) (abstract).
Niemela, O., et al, Gastroenterology, vol. 85, pp. 254–259 (1983).
Bickel, M., et al., J. of Hepatology, vol. 13 (Suppl. 3), pp. S26–S34 (1991).
Siegers, C., in Liver Drugs, Testa, B. and Perrissoud, D., eds., pp. 15–29, CRC Press (1988).
Kivirikko, K. I., et al., in Liver Drugs, Testa, B. and Perrissoud, D, eds., pp. 193–223, CRC Press (1988).
Boker, K., et al., J. of Hepatology, vol. 13 (Suppl. 3), pp. S35–S40 (1991).
Bickel, M., et al., "Effects of a Prolyl 4–Hydroxylase Inhibitor on Collagen Synthesis in Different Rat Organs," European Digestive Disease Week (1991).
Popper, H., in The Liver: Biology and Pathobiology, Second Edition, Raven Press, Ltd., New York, 1988, pp. 1087–1103.
Schuppan, D., et al., J. Clin. Invest. vol. 78, Jul. 1986, pp. 241–248.
Bickel, M., et al., Gastroenterology 1990, vol. 98, A 570.
Hahn, E. G., et al., in Liver Drugs, CRC Press, Boca Raton, Florida, 1988, pp. 233–237.
Bickel, M., et al., J. of Hepatology, in press.
Rouiller, C., in The Liver, vol. 2, Academic Press, New York, 1984, pp. 335–476.
Müller, W., et al., "Influence of the posttranslational hydroxylation step on the secretion of Clq, a subcomponent of the first component of complement, by macrophages", Immunologie, 155:47 (1978).
Müller, W., et al., "Reversible Inhibition of Clq Release From Guinea Pig Macrophages by 2,2'–Dipyridyl", FEBS Letters, 90:218–222 (1978).
Hirakata, T., et al., "On the Reaction of Pyridinecarboxylic Acids with p–Toluenesulfonamide", J. Pharm. Soc. Japan, 77:219 (1956).
Majamaa, K., et al., "The 2–oxoglutarate binding site of prolyl 4–hydroxylase", Eur. J. Biochem., 138:239–245 (1984).
Tschank, G, et al., "Pyridinecarboxylates, the first mechanism–derived inhibitors for prolyl 4–hydroxylase, selectively suppress cellular hydroxyprolyl biosynthesis", Biochem. J., 248:625–633 (1987).

*Primary Examiner*—Jane Fan
*Attorney, Agent, or Firm*—Finnegan, Henderson, Farabow, Garrett & Dunner

[57] ABSTRACT

The invention relates to N,N'-bis(alkoxyalkyl)-pyridine-2,4-dicarboxylic acid diamides of the formula I

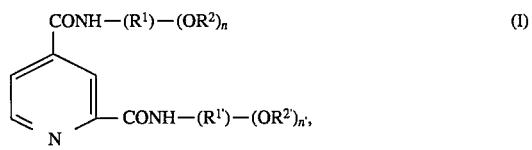

wherein $R^1$, $R^2$, n, $R^{1'}$, $R^{2'}$ and n' have the meanings given. The compounds inhibit proline hydroxylase and lysine hydroxylase and are suitable as fibrosuppressants and immunosuppressants.

14 Claims, 1 Drawing Sheet

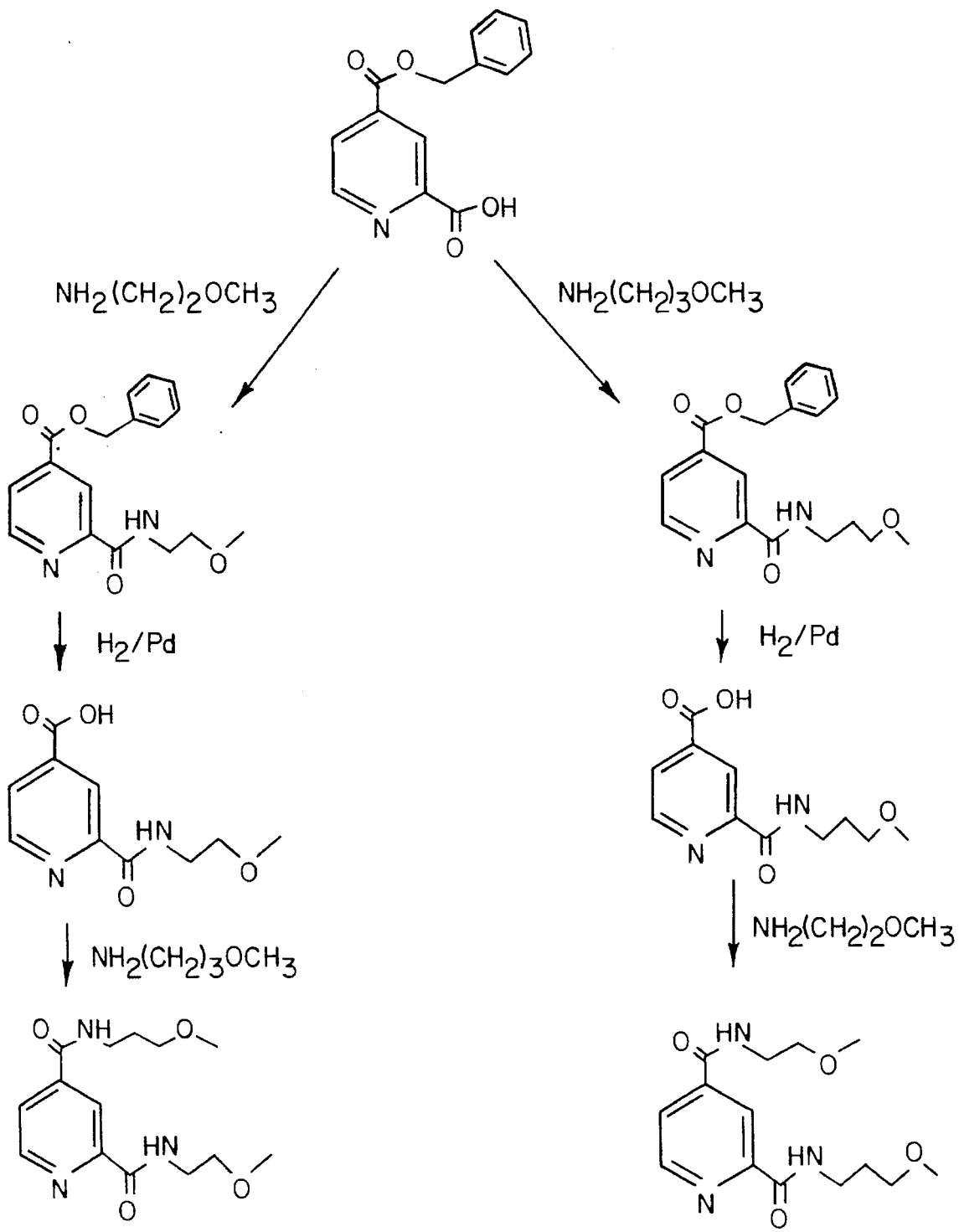

N,N'-BIS(ALKOXYALKYL)-PYRIDINE-2,4-DICARBOXYLIC ACID DIAMIDES

This application is a continuation of prior application Ser. No. 08/139,073 filed Oct. 21, 1993, now abandoned, which is a continuation of application Ser. No. 07/875,191 filed Apr. 27, 1992, abandoned, which is a continuation of application Ser. No. 07/553,590 filed Jul. 18, 1990, abandoned.

DESCRIPTION

Compounds which inhibit proline hydroxylase and lysine hydroxylase cause a very selective inhibition of collagen biosynthesis by influencing the collagen-specific hydroxylation reactions. In the course of these, protein-bound proline or lysine is hydroxylated by the enzymes proline hydroxylase or lysine hydroxylase. If this reaction is suppressed by inhibitors, a non-functional, hypohydroxylated collagen molecule is formed, which can be released by the cells into the extracellular space in only a small amount. The hypohydroxylated collagen also cannot be incorporated into the collagen matrix and is very easily degraded by proteolysis. As a consequence of these effects, the amount of extracellularly deposited collagen overall is reduced.

It is known that the inhibition of proline hydroxylase by known inhibitors, such as α, α'-dipyridyl, leads to an inhibition of the $Cl_q$ biosynthesis of macrophages (W. Müller et al., FEBS Lett. 90 (1978), 218; and Immunbiology 155 (1978) 47). This results in a failure of the classical route of complement activation. Inhibitors of proline hydroxylase therefore also act as immunosuppressants, for example in cases of immune complex diseases.

It is known that proline hydroxylase is inhibited effectively by pyridine-2,4- and -2,5-dicarboxylic acid (K. Majamaa et al., Eur. J. Biochem. 138 (1984) 239–245). However, in the cell culture these compounds are effective as inhibitors only in very high concentrations (Tschank, G. et al., Biochem. J. 238, 625–633, 1987).

German Patent A-3,432,094 describes pyridine-2,4- and -2,5-dicarboxylic acid diesters having 1–6 carbon atoms in the ester alkyl part as pharmaceuticals for inhibition of proline hydroxylase and lysine hydroxylase.

However, these lower alkylated diesters have the disadvantage that they are split too rapidly in the organism to give the acids and do not arrive at their site of action in the cell in a sufficiently high concentration, and are therefore of little suitability for possible administration as pharmaceuticals.

South African Patent Document 88-0896, German Patent A-3,703,962 and German Patent A-3,703,963 describe, in general form, mixed ester/amides, higher alkylated diesters and diamides of pyridine-2,4- and -2,5-dicarboxylic acid which effectively inhibit collagen biosynthesis in the animal model.

South African Patent Document 88-0896 thus describes, inter alia, the synthesis of N,N'-bis(2-methoxyethyl)-pyridine-2,4-dicarboxylic acid diamide (III)

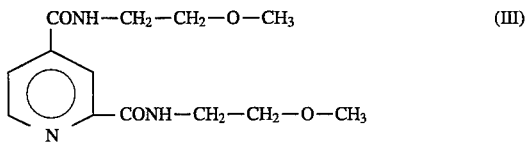

and

N,N'-bis (3-isopropoxypropyl)-pyridine-2,4-dicarboxylic acid diamide (IV)

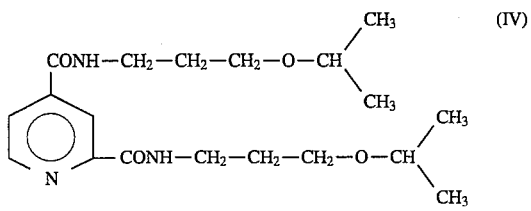

An improved process for the preparation of N,N'-bis(2-methoxyethyl)-pyridine-2,4-dicarboxylic acid diamide (III) is proposed in German Patent Applications P 38 26 471.4 and P 38 28 140.6.

The enteral absorbability of many of the compounds described in South African Patent Document 88-0896 is still unsatisfactory, however, so that there is a need to provide compounds which effectively inhibit proline hydroxylase and lysine hydroxylase after oral administration even in low dosages.

It has been found that compounds of the formula I

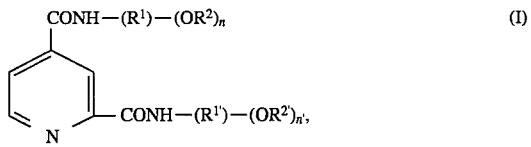

wherein
R¹ denotes linear or branched $C_1-C_4$-alkanediyl,
R² denotes unbranched $C_1-C_4$-alkyl or hydrogen,
n denotes 1 or 2 and
R¹', R²' and n' have the same meanings as R¹, R² and n, R¹ and R¹', and R² and R²' and n and n' being identical or different,
and physiologically tolerated salts thereof, excluding N,N'-bis(2-methoxyethyl)-pyridine-2,4-dicarboxylic acid diamide and N,N'-bis(2-hydroxyethyl)-pyridine-2,4-dicarboxylic acid diamide, achieve the abovementioned object. In comparison with the compounds N,N'-bis(2-methoxyethyl)-pyridine-2,4-dicarboxylic acid diamide and N,N'-bis(3-isopropoxypropyl)-pyridine-2,4-dicarboxylic acid diamide described in South African Patent Document 88-0896, the compounds of the formula I have both a better pharmacological activity and a better enteral absorbability.

The invention furthermore relates to a process for the preparation of N,N'-bis-( alkoxyalkyl )-pyridine-2,4-dicarboxylic acid diamides of the formula I

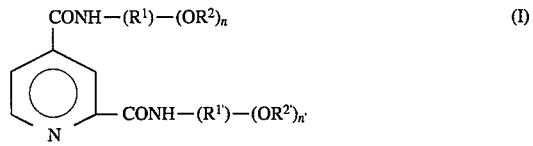

wherein
R¹ denotes linear or branched $C_1-C_4$-alkanediyl,
R² denotes unbranched $C_1-C_4$-alkyl or hydrogen,
n denotes 1 or 2 and
R¹', R²' and n' have the same meanings as R¹, R² and n, R¹ and R¹', and R² and R²' and n and n' being identical or different, excluding N,N'-bis(2-methoxyethyl)-pyridine-2,4-dicarboxylic acid diamide and N,N'-bis (2-hydroxyethyl)-pyridine-2,4-dicarboxylic acid diamide,
which comprises reacting a pyridine-2,4-dicarboxylic acid halide with an alkoxyalkylamine or hydroxyalkylamine.

The invention likewise relates to a process for the preparation of N,N'-bis-(alkoxyalkyl)-pyridine-2,4-dicarboxylic acid diamides of the formula I

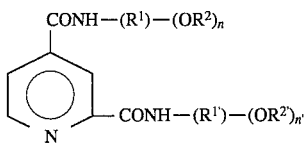

(I)

wherein
$R^1$ denotes linear or branched $C_1$–$C_4$-alkanediyl,
$R^2$ denotes unbranched $C_1$–$C_4$-alkyl or hydrogen,
n denotes 1 or 2 and
$R^{1'}$, $R^{2'}$ and $n'$ have the same meanings as $R^1$, $R^2$ and n, $R^1$ and $R^{1'}$, and $R^2$ and $R^{2'}$ and n and n' being identical or different,
which comprises first
A) 1. adding at least two equivalents of a halogenating agent to pyridine-2,4-dicarboxylic acid and
2. dissolving at least 2 equivalents of a hydroxyalkylamine or alkoxyalkylamine of the formula II or II'

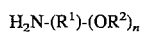   (II)

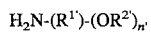   (II')

in which
$R^1$ and $R^{1'}$ denote linear or branched $C_1$–$C_4$-alkanediyl,
$R^2$ and $R^{2'}$ denote unbranched $C_1$–$C_4$-alkyl or hydrogen,
n and n' denote 1 or 2 and
$R^1$ and $R^{1'}$, $R^2$ and $R^{2'}$ and n and n' are identical or different, but II and II' are different, in a solvent
and then reacting the solution prepared according to 1. with the solution prepared according to 2., or
B) converting the resulting N,N'-bis(alkoxyalkyl)-pyridine-2,4-dicarboxylic acid diamide into the bis(hydroxyalkyl) compound, or
C) reacting the pyridine-2,4-dicarboxylic acid halide prepared according to A) 1. with a substituted or unsubstituted benzyl alcohol to give the benzyl pyridine-2,4dicarboxylate, hydrolyzing the benzyl ester selectively in the 2-position of the pyridine, converting the free carboxylic acid in the 2-position into the acid halide again in accordance with process variant A) 1. and adding a solution prepared according to A) 2. using a compound of the formula II' to the compound thus obtained, a pyridine-4-(carboxylic acid benzyl ester)-2-carboxylic acid amide being formed, and then splitting off the benzyl protective group in the 4-position by hydrogenolysis, converting the free carboxylic acid into the acid chloride again in accordance with process variant A) 1., and subsequently adding a solution prepared according to A) 2. using a compound of the formula II, an unsymmetrically substituted compound of the formula I being formed, and if appropriate then converting the resulting compound of the formula I into its physiologically tolerated salt.

In the process for the preparation of the compounds of the formula I, the pyridine-2,4-dicarboxylic acid commercially available as a starting substance is suspended in a solvent, such as toluene, and a halogenating agent, preferably a chlorinating agent, such as, for example, $SOCl_2$, is added at room temperature. 2–3 equivalents, preferably 2.5 equivalents, of a halogenating agent, based on the molar amount of pyridine-2,4-dicarboxylic acid employed, are used. The resulting reaction mixture is heated at 90°–110° C., preferably at 100° C., until no further evolution of gas is to be observed and a clear solution has formed. 10% of the solution is then evaporated off—preferably under a high vacuum (down to about $10^{-3}$ mm Hg)—and the resulting carboxylic acid halide is reacted further.

2–4 times the molar amount of commercially available alkoxyalkylamine or hydroxyalkylamine, based on the molar amount of pyridine-2,4-dicarboxylic acid employed, is now dissolved in a solvent, such as toluene, and 2–4 times the molar amount of a base, such as triethylamine, is preferably added. The carboxylic acid halide is reacted with the alkoxyalkylamine or the hydroxyalkylamine. This is preferably done by adding the solution of the alkylamine mentioned dropwise to the dissolved pyridine-2,4-dicarboxylic acid halide. However, it is also possible to add the solution of the carboxylic acid halide dropwise to the solution of the alkoxyalkylamine or hydroxyalkylamine. The addition is carried out at a temperature of −5° to +5° C., preferably at 0° C. The reaction mixture can then be afterreacted, for example, by warming it to room temperature and subsequently stirring it for a further 2–5 hours, preferably 3 hours. The resulting product is then acidified in order to remove excess hydroxy- or alkoxyalkylamine from the desired product. The acidification can be carried out, for example, with 0.2 molar citric acid. The organic phase is then separated off and washed with water. The organic phase is subsequently dried—preferably over magnesium sulfate—and finally freed from the solvent. On removal of the solvent, the product is obtained as a white solid or as an oil.

To prepare the N,N'-bis(hydroxyalkyl )-pyridine-2,4-dicarboxylic acid diamides, a procedure is preferably followed in which a corresponding bis(alkoxyalkyl)diamide, preferably bis(methoxyalkyl)diamide, is converted into the corresponding bis(hydroxyalkyl)diamide by processes which are known from the literature, for example using boron tribromide.

Unsymmetrically substituted compounds of the formula I can be synthesized, for example, as follows: reaction of a pyridine-2,4-dicarboxylic acid halide, preferably the chloride, with substituted or unsubstituted benzyl alcohol to give benzyl pyridine-2,4-dicarboxylate, subsequent selective hydrolysis of the ester in the 2-position (for example in the presence of a copper catalyst, Acta Helv. 44, 1963, page 637), conversion of the free acid in the 2-position into the acid halide, reaction with a compound of the formula (II') to give the pyridine-4-(carboxylic acid benzyl ester)-2-carboxylic acid amide, splitting off of the remaining benzyl protective group by hydrogenolysis (for example with $H_2$/Pd, see Houben-Weyl Volume IV/1c (1980), pages 381–82) and subsequent conversion of the free acid in the 4-position of the pyridine ring into the acid halide. The acid halide can now be converted into the mixed diamide (I) with an amine II (see Figure).

If appropriate, the products can be worked up, for example, by extraction or by chromatography, for example over silica gel. The product isolated can be recrystallized and if appropriate reacted with a suitable acid to give a physiologically tolerated salt. Examples of possible suitable acids are: mineral acids, such as hydrochloric and hydrobromic acid as well as sulfuric, phosphoric, nitric or perchloric acid, or organic acids, such as formic, acetic, propionic, succinic, glycolic, lactic, malic, tartaric, citric, maleic, fumaric, phenylacetic, benzoic, methanesulfonic, toluenesulfonic, oxalic, 4-aminobenzoic, naphthalene-1,4-disulfonic or ascorbic acid.

The compounds of the formula I can be used as medicaments in the form of pharmaceutical preparations which contain them, if appropriate together with tolerated pharmaceutical excipients. The compounds can be used as medicines, for example in the form of pharmaceutical preparations which contain these compounds as a mixture with a pharmaceutical, organic or inorganic excipient suitable for enteral, percutaneous or parenteral administration, such as, for example, water, gum arabic, gelatin, lactose, starch, magnesium stearate, talc, vegetable oils, polyalkylene glycols, vaseline and the like.

The pharmaeutical preparations can be in solid form, for example as tablets, coated tablets, suppositories or capsules; in semi-solid form, for example as ointments, or in liquid form, for example as solutions, suspensions or emulsions. If appropriate, they are sterilized and/or contain auxiliaries, such as preservatives, stabilizers, wetting agents or emulsifiers, salts for modifying the osmotic pressure or buffers. They can also additionally contain other therapeutically active substances.

It has been found that the compounds of the formula I have exceptionally good enteral absorbabilities. The absorbability was investigated on Wistar rats to which the compounds according to the invention were administered intragastrally. The serum level dropped in the first hours after administration of the substance, and after about 5 hours reached a plateau which still fell only slightly. The good absorbability of the substances can be concluded from the initially very high serum level directly after administration of the substances.

The invention is illustrated in more detail below with the aid of examples.

EXAMPLE 1

Pyridine-2,4-dicarboxylic acid bis-N,N'-(methoxypropyl) amide 3 g of pyridine-2,4-dicarboxylic acid are initially introduced into 50 ml of toluene and 1 ml of dimethylformamide, and 2.7 ml of thionyl chloride are added dropwise to the solution. The mixture is heated until no further evolution of gas is to be observed (about 2.5 hours). It is cooled, 5 ml of toluene are distilled off and 4.6 ml of 3-methoxypropylamine and 5 ml of triethylamine are added dropwise to the solution. After the solution has been stirred at room temperature for 4 hours, it is evaporated, the residue is taken up in water and the mixture is extracted 4 times with methylene chloride. The combined organic phases are dried over magnesium sulfate and evaporated. The crude product is chromatographed with silica gel (solvent: ethyl acetate).
Yield: 4.3 g; oil
$^1$H-NMR (CDCl$_3$): δ=1.6–2.3 (4H, m); 3.2–3.8 (14H, m); 7.8–8.0 (1H, m); 8.3–8.5 (1H, m); 8.6–8.8 (1H, m).

EXAMPLE 2

Pyridine-2,4-dicarboxylic acid bis-N,N'-(ethoxypropyl)amide

For instructions see Example 1; amine component: ethoxypropylamine
Yield: 4.5 g, melting point: 46°–48° C.
$^1$H-NMR (CDCl$_3$): δ=1.3 (6H, tr); 1.7–2.1 (4H, m); 3.3–3.8 (12H, m); 7.8–8.0 (1H, m); 8.4–8.5 (1H, m); 8.5–8.8 (1H, m).

EXAMPLE 3

Pyridine-2,4-dicarboxylic acid bis-N,N'-(2-dimethoxyethyl) amide

For instructions see Example 1; amine component: 2-dimethoxyethylamine
Yield: 1.6 g (from 3 g of pyridine-2,4-dicarboxylic acid), oil
$^1$H-NMR (CDCl$_3$): δ=3.4 (12H, s); 3.7 (4H, m); 4.5 (2H, m); 7.9–8.0 (1H, m); 8.4–8.5 (1H, m); 8.7–8.8 (1H, m).

EXAMPLE 4

Pyridine-2,4-dicarboxylic acid bis-N,N'-(2-methoxyisopropyl)amide

For instructions see Example 1; amine component: 2-methoxyisopropylamine;
Yield: 3.3 g (from 3 g of pyridine-2,4-dicarboxylic acid), oil $^1$H-NMR (CDCl$_3$): δ=1.3 (6H, d); 3.2 (6H, s); 3.5 (4H, d); 4.4 (2H, m); 7.9–8.0 (1H, m); 8.4–8.5 (1H, m); 8.7–8.8 (1H, m).

EXAMPLE 5

Pyridine-2,4-dicarboxylic acid bis-N,N'-(2-ethoxyethyl)amide

For instructions see Example 1; amine component: ethoxyethylamine,
Yield: 7.8 g (from 10 g of pyridine-2,4-dicarboxylic acid), melting point: 42°–44° C.
$^1$H-NMR (CDCl$_3$): δ=1.2 (3H, tr); 3.3–3.8 (12H, qu. and m); 7.9 (1H, m); 8.4–8.5 (1H, m); 8.7–8.8 (1H, m).

EXAMPLE 6

Pyridine-2,4-dicarboxylic acid bis-N,N'-(3-hydroxyethyl)amide 0.5 g of pyridine-2,4-dicarboxylic acid bis-N,N'-(3-methoxyethyl)amide are dissolved in 10 ml of methylene chloride, and boron tribromide (11 ml, 1 molar solution in methylene chloride) is added dropwise at −78° C. When the addition has ended, the mixture is allowed to come to room temperature and is subsequently stirred for 3 hours. It is poured onto 100 ml of saturated bicarbonate solution and extracted 3 times with ethyl acetate. The combined organic phases are dried with magnesium sulfate and evaporated. The crude product is chromatographed on silica gel.
Yield: 0.45 g; oil
$^1$H-NMR (CDCl$_3$): δ=1.5–2.2 (4H, m); 3.4 (4H, m); 3.6 (4H, m); 7.9–8.0 (1H, m); 8.4–8.5 (1H, m); 8.7–8.8 (1H, m).

EXAMPLE 7a

Pyridine-2,4-dicarboxylic acid dibenzyl ester 30g of pyridine-2,4-dicarboxylic acid are converted into the acid chloride using 30 ml of thionyl chloride analogously to Example 1 and the acid chloride is reacted with 43.8 g of benzyl alcohol. The product is recrystallized from diisopropyl ether.
Yield: 42.1 g Melting point 63°–65° C.

EXAMPLE 7b

Pyridine-2-(carboxylic acid)-4-carboxylic acid benzyl ester 40 g of pyridine-2,4-dicarboxylic acid dibenzyl ester from Example 7a are added to a suspension of 27.8 g of copper-II nitrate in 700 ml of methanol. The mixture is boiled under reflux for one hour and, after cooling, the copper complex is filtered off. The complex is suspended in dioxane and carbon disulfide is passed in. The copper sulfide which has precipitated is filtered off and the organic phase is concentrated. The product is stirred with petroleum ether.
Yield: 25.3 g Melting point 113°–115° C.

EXAMPLE 7c

Pyridine-2-[(3-methoxypropyl)-carboxylic acid amide]-4-carboxylic acid benzyl ester 3.9 g of pyridine-2-(carboxylic acid)-4-carboxylic acid benzyl ester from Example 7b are converted into the acid chloride using 1.2 ml of thionyl chloride analogously to Example 1 and the acid chloride is reacted with 3-methoxypropylamine to give the amide. For purification, the product is chromatographed over silica gel using a mixture of cyclohexane/ethyl acetate (1:1).
Yield: 4.3 g Oil

EXAMPLE 7d

Pyridine-4-(carboxylic acid)-2-(3-methoxypropyl)-carboxylic acid amide 4.3 g of the compound from Example 7c are dissolved in 100 ml of dioxane and hydrogenated using 500 mg of palladium/charcoal (10% strength) catalyst under normal pressure for 4 hours. When the uptake of hydrogen has ended, the catalyst is filtered off with suction and the solvent is stripped off.
Yield: 3.5 g Melting point 124°–126° C.

EXAMPLE 7e

Pyridine-4-[carboxylic acid-(2-methoxyethyl)-amide]-2-carboxylic acid(3-methoxypropyl)-amide 1.8 g of the compound from Example 7d are converted into the acid chloride using 0.6 ml of thionyl chloride in accordance with Example 1 and the acid chloride is then reacted with 2-methoxyethylamine. For purification, the product is chromatographed over silica gel using a mixture of methylene chloride/methanol (20:1).
Yield: 1.0 g Oil
$^1$H-NMR (CDCl$_3$): δ=1.9–2.0 (2H, qui); 3.4 (6H, s); 3.5–3.7 (8H, m); 6.9 (1H, s, br); 8.0 (1H, dd); 8.4 (1H, s, br); 8.5 (1H, s); 8.7 (1H, d).

EXAMPLE 8

Pyridine-2-[carboxylic acid-(2-methoxyethyl)-amide]-4-carboxylic acid(3-methoxypropyl)-amide The compound according to Example 8 is prepared analogously to Examples 7a–e by using 2-methoxyethylamine in the reaction step of Example 7c and 3-methoxypropylamine in the reaction step of Example 7e.
Melting point: 69°–72° C.
$^1$H-NMR (CDCl$_3$): δ=1.9–2.0 (2H, qui); 3.4 (3H, s); 3.45 (3H, s); 3.6–3.7 (8H, m); 7.4 (1H, br); 7.9 (1H, dd); 8.3 (1H, br); 8.4 (1H, d); 8.7 (1H, d).

EXAMPLE 9

Enteral absorbability

Female Wistar rats of about 150 g body weight are given an intragastral administration of 50 mg/kg of the substance under investigation by means of a stomach probe.

In each case 4 rats are anesthetized after 5; 10; 15; 30; 60; 120; 180 and 240 minutes and exsanguinated via the Vena Cava. The blood is centrifuged immediately and the compound administered is extracted from the serum using ether. After the ether has been evaporated, the residue is taken up in 100 ml of mobile phase. The mobile phase consists of 0.05M phosphoric acid and acetonitrile (4:1). 50 μl of this sample are injected into a high performance liquid chromatography column. Detection is performed under UV of 200 nm with a retention time of 2.2 minutes. The results are documented in Table 1.

TABLE 1

Serum levels of the compounds according to the invention from Examples 1–3 after administration of 50 mg/kg perorally

| Time (minutes) | Substance from Example 1 x̄ SD | Substance from Example 2 x̄ SD | Substance from Example 3 x̄ SD |
|---|---|---|---|
| 5 | 45.3 ± 15.4 | 51.4 ± 11.2 | 8.9 ± 3.1 |
| 10 | 49.8 ± 3.6 | 39.2 ± 4.0 | 11.5 ± 0.6 |
| 15 | 39.9 ± 11.0 | 29.4 ± 6.7 | 14.7 ± 1.9 |
| 30 | 28.1 ± 3.2 | 15.2 ± 5.6 | 10.7 ± 1.9 |
| 60 | 9.4 ± 5.5 | 1.4 ± 1.0 | 11.3 ± 1.5 |
| 120 | 0.3 ± 0.3 | <DL | 5.5 ± 0.9 |
| 180 | <DL | <DL | 2.9 ± 0.5 |
| 240 | <DL | <DL | 1.7 ± 0.4 | x̄ = mean value of 4 measurements
SD = standard deviation
<DL = below the detection limit

EXAMPLE 10

Pharmacological activity

To demonstrate the effective inhibition of proline hydroxylase and lysine hydroxylase by the compounds according to the invention, the hydroxyproline concentrations in the liver and the 7s-(IV)-collagen concentrations in the serum of
a) untreated rats (control)
b) rats to which carbon tetrachloride had been administered (CCl$_4$ control)
c) rats to which first CCl$_4$ and then a compound according to the invention had been administered were measured (this test method is described by Rouiller, C., experimental toxic injury of the liver; in The Liver, C. Rouiller, Volume 2, pages 335–476, New York, Academic Press, 1964).

The action potency of the compounds according to the invention was determined as the percentage inhibition of the liver hydroxyproline synthesis and serum 7s-(IV)collagen synthesis following oral administration in comparison with control animals to which only carbon tetrachloride had been administered (CCl$_4$ control). The results are shown in Table 2. The compounds from Examples 19 and 20 of South African Patent Document 88-0896 (N,N'-bis(2-methoxyethyl)-pyridine-2,4-dicarboxylic acid diamide and N,N'-bis(3-isopropoxypropyl)-pyridine-2,4-dicarboxylic acid diamide) are likewise also shown as comparison substances. Surprisingly, the compounds according to the invention show a better activity, even after oral administration, than the intraperitoneally administered compound from Example 19 of South African Patent Document 88-0896.

TABLE 2

| Substance from Example | Dosage | Liver hydroxyproline [% inhibition] | Serum 7s-(IV)-collagen [% inhibition] | Administration |
|---|---|---|---|---|
| 1 | 2 × 2 mg | 62 | 28 | p.o. |
|   | 2 × 10 mg | 90 | 67 | p.o. |
| 2 | 2 × 2 mg | 25 | 2 | p.o. |
|   | 2 × 10 mg | 60 | 35 | p.o. |
| 19 (from SA-88-0896) | 2 × 25 mg | 55 | 48 | i.p. |
| 20 (from SA-88-0896) | 2 × 25 mg | 49 | 11 | p.o. |

TABLE 2-continued

| Substance from Example | Dosage | Liver hydroxy-proline [% inhibition] | Serum 7s-(IV)-collagen [% inhibition] | Administration |
|---|---|---|---|---| p.o. = peroral
i.p. = intraperitoneal.

We claim:

1. An N, N'-bis(alkoxyalkyl)-pyridine-2,4,-dicarboxylic acid diamide of the formula I

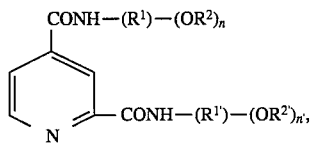 (I)

wherein
$R^1$ denotes linear or branched $C_1$–$C_4$-alkanediyl,
$R^2$ denotes unbranched $C_1$–$C_4$-alkyl or hydrogen,
n denotes 1 or 2 and
$R^{1'}$, $R^{2'}$ and n' have the same meanings as $R^1$, $R^2$ and n, $R^1$ and $R^{1'}$, $R^2$ and $R^{2'}$, and n and n' being identical or different,
or a physiologically tolerated salt thereof, excluding N,N'-bis(2-methoxyethyl)-pyridine-2,4,-dicarboxylic acid diamide, N,N'-bis(2-hydroxyethyl)-pyridine-2,4-dicarboxylic acid diamide.

2. A compound of the formula I as claimed in claim 1, in which in each case $R^1$ and $R^{1'}$, $R^2$ and $R^{2'}$ and n and n' have the same meaning.

3. A compound of the formula I as claimed in claim 1, in which the substituents -($R^1$)-($OR^2$)n and -($R^{1'}$)-($OR^{2'}$)n' are different.

4. A compound of the formula I as claimed in claim 1, in which
$R^1$ denotes linear or branched $C_1$–$C_3$-alkyl and
$R^2$ denotes unbranched $C_1$–$C_2$-alkyl or hydrogen.

5. The compound of the formula

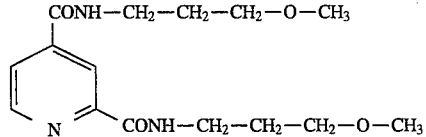

or one of its physiologically tolerated salts.

6. The compound of the formula

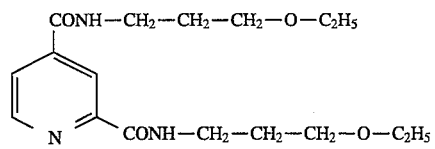

or one of its physiologically tolerated salts.

7. The compound of the formula

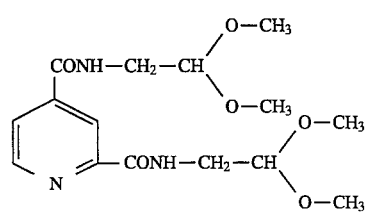

or one of its physiologically tolerated salts.

8. The compound of the formula

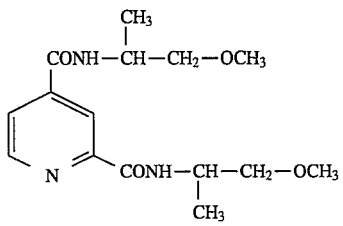

or one of its physiologically tolerated salts.

9. The compound of the formula

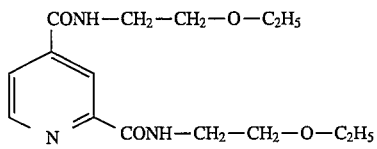

or one of its physiologically tolerated salts.

10. The compound of the formula

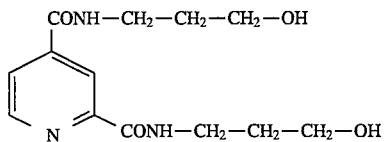

or one of its physiologically tolerated salts.

11. The compound of the formula

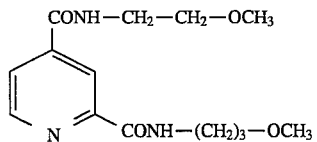

or one of its physiologically tolerated salts.

12. The compound of the formula

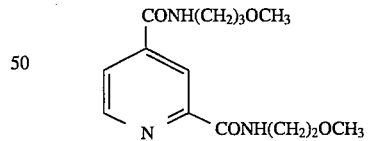

or one of its physiologically tolerated salts.

13. A method for inhibiting proline hydroxylase and lysine hydroxylase in a mammal comprising administering to a mammal a pharmaceutically effective amount of a compound as claimed in claim 1.

14. A method for fibrosuppression in a mammal comprising administering to a mammal a pharmaceutically effective amount of a compound as claimed in claim 1.

* * * * *